United States Patent
Wohlschlager et al.

(10) Patent No.: US 11,666,268 B2
(45) Date of Patent: Jun. 6, 2023

(54) DEVICE FOR MEASURING UTERINE CONTRACTIONS AND FETAL HEART RATE

(71) Applicant: KONINKLIJKE PHILIPS N.V., Eindhoven (NL)

(72) Inventors: Markus Silvester Wohlschlager, Sindelfingen (DE); Hansjoerg Geywitz, Kusterdingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 497 days.

(21) Appl. No.: 16/753,424

(22) PCT Filed: Oct. 2, 2018

(86) PCT No.: PCT/EP2018/076740
§ 371 (c)(1),
(2) Date: Apr. 3, 2020

(87) PCT Pub. No.: WO2019/068684
PCT Pub. Date: Apr. 11, 2019

(65) Prior Publication Data
US 2020/0315521 A1 Oct. 8, 2020

(30) Foreign Application Priority Data
Oct. 6, 2017 (EP) ................ EP17195205.4

(51) Int. Cl.
*A61B 5/00* (2006.01)
*A61B 5/024* (2006.01)

(52) U.S. Cl.
CPC ........ *A61B 5/4362* (2013.01); *A61B 5/02411* (2013.01); *A61B 5/4356* (2013.01);
(Continued)

(58) Field of Classification Search
CPC .... A61B 2562/0204; A61B 2562/0233; A61B 2562/0247; A61B 5/02411; A61B 5/033;
(Continued)

(56) References Cited

U.S. PATENT DOCUMENTS

| 4,324,259 A | 4/1982 | Wright |
| 5,807,271 A | 9/1998 | Tayebi et al. |

(Continued)

FOREIGN PATENT DOCUMENTS

| EP | 300069 A1 | 1/1989 |
| WO | 2005110236 A1 | 11/2005 |
| WO | 2015082987 A1 | 6/2015 |

OTHER PUBLICATIONS

International Search Report and Written Opinion, International Application No. PCT/EP2018/076740, dated Jan. 11, 2019.

*Primary Examiner* — George Manuel (57) ABSTRACT

There is provided a device (100) for placement on the abdomen (102) of a subject to measure uterine contractions of the subject and a fetal heart rate. The device (100) comprises a rigid base (104) for placement on the abdomen (102) of the subject and a cover (106) configured to connect to the rigid base (104). The cover (106) comprises a flexible portion moveable in response to uterine contractions of the subject. The device (100) further comprises a fetal heart rate sensor (108) mounted on the rigid base (104) and configured to measure the fetal heart rate. The device (100) also comprises a uterine contractions sensor (110) located within the device (100) and configured to measure the uterine contractions of the subject.

15 Claims, 6 Drawing Sheets

(52) U.S. Cl.
CPC .... *A61B 5/6823* (2013.01); *A61B 2562/0204* (2013.01); *A61B 2562/0233* (2013.01); *A61B 2562/0247* (2013.01)

(58) Field of Classification Search
CPC ... A61B 5/4356; A61B 5/4362; A61B 5/6823; A61B 8/02; A61B 8/0866; A61B 8/4227
See application file for complete search history.

(56) References Cited

U.S. PATENT DOCUMENTS

| | | |
|---|---|---|
| 6,879,858 B1 | 4/2005 | Adams |
| 7,758,522 B2 | 7/2010 | Pandit |
| 2006/0149168 A1 | 7/2006 | Czarnek |
| 2008/0161689 A1 | 7/2008 | Pandit |
| 2013/0261464 A1 | 10/2013 | Singh et al. |
| 2013/0310710 A1 | 11/2013 | Eswaran et al. |
| 2013/0331704 A1 | 12/2013 | Salzman |
| 2014/0350397 A1 | 11/2014 | Lewis, Jr. et al. |
| 2016/0157717 A1 | 6/2016 | Gaster |
| 2016/0270685 A1 | 9/2016 | Oz et al. |
| 2016/0317091 A1 | 11/2016 | Olukoya et al. |
| 2016/0331299 A1* | 11/2016 | Cline .................. A61B 5/721 |

* cited by examiner

DEVICE FOR MEASURING UTERINE CONTRACTIONS AND FETAL HEART RATE

This application is the U.S. National Phase application under 35 U.S.C. § 371 of International Application No. PCT/EP2018/076740, filed on 2 Oct. 2018, which claims the benefit of European Application Serial No. 17195205.4, filed 6 Oct. 2017. These applications are hereby incorporated by reference herein.

FIELD OF THE INVENTION

The invention relates to the field of healthcare monitoring and, in particular, to a device for placement on an abdomen of a subject for measuring uterine contractions of the subject and a fetal heart rate.

BACKGROUND TO THE INVENTION

In obstetrics, especially during labour and delivery, two medical parameters are important to assess the wellbeing of a fetus. These two parameters are fetal heart rate and uterine contractions (or uterine activity). For the determination of the fetal condition, the simultaneous recording of both parameters over time is important. Modern medical devices use external transducers to derive these parameters. Typically, an ultrasound Doppler (US) transducer and a strain gauge transducer are used for this purpose, where the ultrasound Doppler transducer comprises a sensor that measures the fetal heart rate and the strain gauge transducer comprises a sensor that measures the uterine contractions.

When measuring uterine contractions and fetal heart rate simultaneously, the optimum position on the abdomen for yielding the best signal quality is typically not identical for the two measurements. For example, the fetal heart rate transducer must be placed directly over the fetal heart, because the heart rate signal is often contained in a noisy received ultrasound signal. For this reason, the fetal heart rate transducer and the uterine contractions transducer are traditionally kept separated to allow individual adjustment for optimisation. Having the two transducer separated means that independent elastic belts are required to fix the transducer in place on the abdomen. However, the placement and attachment of the belts is time consuming and inconvenient for the expectant mother.

It would be beneficial to reduce the number of transducer and, ideally, capture the most important parameters with a single transducer. For example, this would be more comfortable for the expectant mother, require less technical components, and thus lower cost. However, a problem associated with combining the two measurement principles is that the requirements for the housing design and the optimal transducer positioning for each are incompatible with one another. An ultrasonic transducer that measures fetal heart rate, for example, requires a housing base on which piezoelectric elements can be glued. The size of the available sound field is important in order to cover a homogenous volume of observation. On the other hand, the size of the sensing area of a tocodynamometer (toco) transducer that measures uterine contractions directly correlates with the sensitivity and should therefore be adjustable. Any lack of sensitivity (for example, in the case of an extended fat layer) can be compensated by a protruding feeler pin.

However, a protruding feeler pin leads to pressure marks, skin irritations and physical discomfort. Also, the mechanical arrangement of the piezoelectric elements on the base of the transducer is fixed and cannot be easily changed. Thus, any constructive changes resulting from the inclusion of a uterine contraction sensor in the transducer design risk a reduction in the performance of the transducer and also impose a need for validation of the transducer in hospitals. For this reason, it is preferable to avoid any changes or modifications to the mechanical and electrical structure of the housing parts related to the fetal heart rate (or ultrasound) functionality.

EP 0 300 069 discloses an example of a transducer in which modifications to the mechanical and electrical structure of the transducer are made to incorporate a uterine activity sensor in addition to a fetal heart rate sensor. The disclosed transducer comprises a movable base plate carrying piezo-electric crystals for fetal heart rate measurement and a resistive wire strain component for measuring uterine activity. The resistive wire strain component is connected with the movable base plate via a guide plate that transmits mechanical motion sensed by the base plate to the resistive wire strain component to give an indication of the uterine activity.

The resistive wire strain component requires additional mechanical components to be provided in the transducer, which increases the risk of the transducer failing due to there being more components that can potentially fail and also contradicts the requirements for keeping the transducer as small as possible. Moreover, as the base plate carrying piezo-electric crystals for fetal heart rate measurement and a resistive wire strain component for measuring uterine activity are mechanically connected, both of these parts have to be replaced in case of a defect in one of those parts. Also, the mechanical connection of components to the moveable base plate can damage the base plate. The application of aggressive liquids (such as disinfection liquids) can also damage the moveable base plate and may cause a leak in the transducer.

There is thus a need for an improved device for measuring uterine contractions of a subject and a fetal heart rate.

SUMMARY OF THE INVENTION

As noted above, a limitation with existing devices is that it is not possible to combine a fetal heart rate sensor and a uterine contraction sensor in a single device without mechanically connecting the sensors in some way and the devices are thus mechanically complex, with replacement of the entire device required irrespective of whether a defect occurs in only one or in both of the sensors. It would thus be valuable to have an improved device for measuring uterine contractions of a subject and a fetal heart rate, which overcomes the existing problems. Therefore, according to a first aspect of the invention, there is provided a device for placement on the abdomen of a subject to measure uterine contractions of the subject and a fetal heart rate. The device comprises a rigid base for placement on the abdomen of the subject and a cover configured to connect to the rigid base. The cover comprises a flexible portion moveable in response to uterine contractions of the subject. The device also comprises a fetal heart rate sensor mounted on the rigid base and configured to measure the fetal heart rate. The device further comprises a uterine contractions sensor located within the device and configured to measure the uterine contractions of the subject.

In some embodiments, the entire cover may be the flexible portion, or the cover may comprise an aperture across which the flexible portion is disposed, or the flexible portion may extend around the periphery of the cover and may be configured to be connected to the rigid base.

In some embodiments, the uterine contractions sensor may comprise any one or more of: a pressure sensor configured to measure a variation in pressure representative of uterine contractions; an optical sensor configured to measure a variation in light intensity representative of uterine contractions; a capacitive sensor configured to measure a variation in capacitance representative of uterine contractions; and an inductive sensor configured to measure a variation in inductance representative of uterine contractions. In some embodiments, the optical sensor may comprise a light source mounted on the rigid base and positioned to emit light toward the flexible portion and a light detector mounted on the rigid base and positioned to detect light reflected from the flexible portion. In some embodiments, the capacitive sensor may comprise a pair of conductors and the rigid base may comprise one of the pairs of conductors and the cover comprises the other of the pairs of conductors. In some embodiments, the inductive sensor may comprise a coil and a conductive plate. In some embodiments, the inductive sensor may comprise a pair of inductors and the rigid base comprises one of the pairs of inductors and the cover may comprise the other of the pairs of inductors.

In some embodiments, the fetal heart rate sensor may comprise an ultrasound sensor or a microphone. In some embodiments, the device may comprise a plurality of fetal heart rate sensors mounted at different positions on the rigid base. In these embodiments, each fetal heart rate sensor may be configured to measure the fetal heart rate. In some embodiments, the device may comprise a plurality of uterine contractions sensors located at different positions within the device. In these embodiments, each uterine contractions sensor may be configured to measure the uterine contractions.

In some embodiments, the cover may be removable from the rigid base. In some embodiments, the device may be substantially airtight or substantially watertight. In some embodiments, the device may be configured to be held against the abdomen of the subject by a supporting member. In these embodiments, the supporting member may be configured to be worn around the abdomen of the subject and may be further configured to contact with the device to cause movement of the flexible portion in response to the uterine contractions.

In some embodiments, the sensors may be configured to measure the fetal heart rate and the uterine contractions simultaneously.

According to a second aspect, there is provided a method of operating a device, when placed on the abdomen of a subject, to measure uterine contractions of the subject and a fetal heart rate. The device is as described above. The method comprises controlling the fetal heart rate sensor to measure the fetal heart rate and/or controlling the uterine contractions sensor to measure the uterine contractions.

According to a third aspect of the invention, there is provided a computer program product comprising a computer readable medium, the computer readable medium having computer readable code embodied therein, the computer readable code being configured such that, on execution by a suitable computer or processor, the computer or processor is caused to perform the method described above.

According to the aspects and embodiments described above, the limitations of existing devices are addressed. In particular, according to the above-described aspects and embodiments, it is possible to reliably measure both the uterine contractions of the subject and the fetal heart rate in a single device with minimal constructional changes. In this way, the number of devices (and any corresponding securing component such as belts) that need to be used to acquire the two measurements is reduced. This reduces the technical effort required in practice and also minimises discomfort for the subject.

Moreover, the above-described aspects and embodiments make this possible without compromising the monitoring quality. For example, as the cover comprises a flexible portion moveable in response to uterine contractions, the uterine contractions can be measured from this movement without compromising the performance of the fetal heart rate sensor and thus reliable measurements can be acquired from both the fetal heart rate sensor and the uterine contractions sensor, with the two sensors located in a single device. The mechanical arrangement and performance of the fetal heart rate sensor can remain unchanged, even with the uterine contractions sensor located in such a combined device. The fact that the cover of the device comprises the flexible portion, while the base of the device is rigid, means that the base of the device for placement of the abdomen is stronger against aggressive liquids (such as disinfection liquids) and less likely to leak, while the flexible portion of the device is sensitive to uterine contractions that can thus be measured.

Moreover, the use of a non-mechanical sensor (such as a pressure sensor, an optical sensor, a capacitive sensor, and/or an inductive sensor) to measure a variation in a property resulting from the force generated by uterine contractions simplifies the device dramatically and reduces (or even eliminates) the mechanical components that may otherwise be required. This allows the size of the device to be reduced and also minimises the risk of the device encountering mechanical failures.

There is thus provided an improved device for measuring uterine contractions of a subject and a fetal heart rate, which overcomes the existing problems.

BRIEF DESCRIPTION OF THE DRAWINGS

For a better understanding of the embodiments, and to show more clearly how they may be carried into effect, reference will now be made, by way of example only, to the accompanying drawings, in which.

DETAILED DESCRIPTION OF THE EMBODIMENTS

As noted above, there is provided an improved device for measuring uterine contractions of a subject and a fetal heart rate, which overcomes existing problems.

Figure 1A:
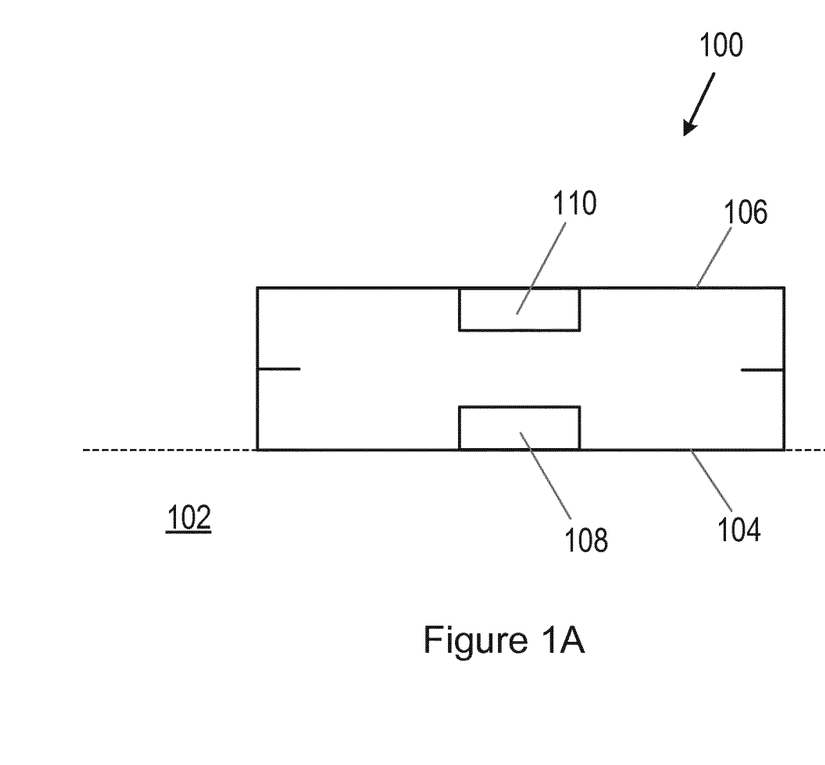
FIG. 1A is a block diagram of a device according to an embodiment.
Figure 1B:
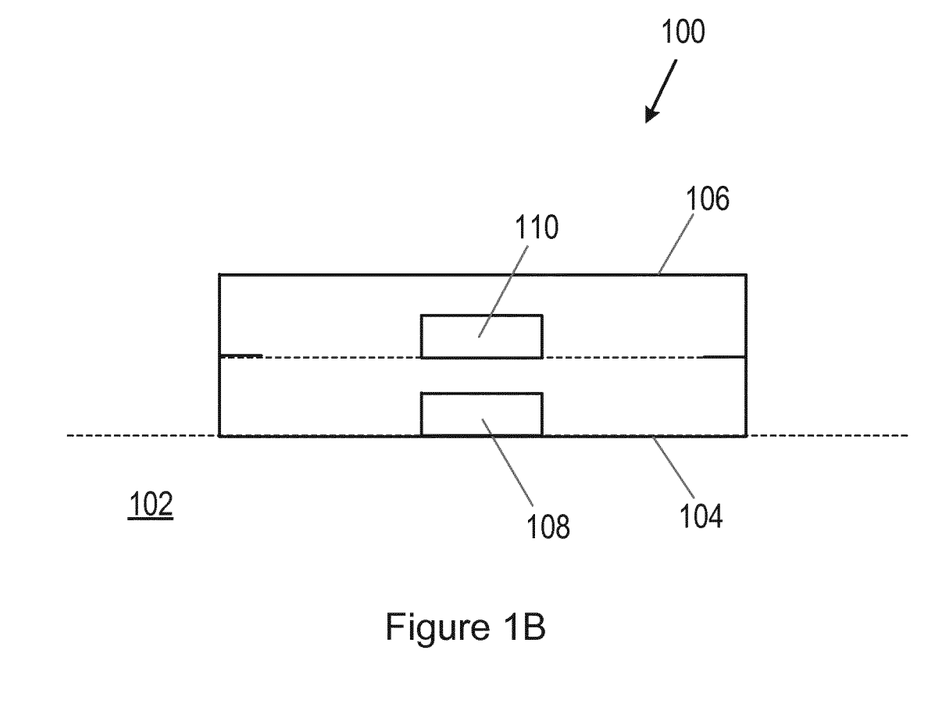
FIG. 1B is a block diagram of a device according to an embodiment.

FIGS. 1A and B illustrate examples of a device 100 for placement on the abdomen 102 of a subject to measure uterine contractions of the subject and a fetal heart rate (FHR) according to an embodiment. The device 100 described herein may also be referred to as a transducer or, in some embodiments, a combined tocodynamometer (toco)

ultrasound transducer. The uterine contractions that are mentioned herein may also be referred to as the uterine activity (UA). A uterine contraction comprises a hardening or tensing of the uterine muscle, which causes a force on the device 100 placed on the abdomen 102 of the subject.

The device 100 described herein can comprise an enclosed volume. The enclosed volume can contain a volume of gas (for example, air). As illustrated in FIGS. 1A and 1B, the device 100 comprises a rigid base (for example, a rigid substrate) 104 for (or adapted for) placement on the abdomen 102 of the subject. The device 100 further comprises a cover (for example, a lid) 106 configured to connect to the rigid base 104. The cover 106 and the rigid base 104 can be two separate parts connectable to one another. Thus, in effect, the device 100 comprises a casing (which may also be referred to as a housing) and the casing comprises the rigid base 104 and the cover 106. The rigid base 104 and the cover 106 together provide the casing (or housing). The cover 106 of the device 100 comprises a flexible portion (which is not depicted in FIGS. 1A and 1B). This flexible portion is moveable in response to uterine contractions of the subject.

When connected to the rigid base 104, the cover 106 is supported by the rigid base 104. The rigid base 104 and the cover 106 are both exposed to the external (or surrounding) environment when connected to each other. In use, the rigid base 104 of the device 100 adapted for placement on the abdomen 102 of the subject is in contact with (or, more specifically, in direct contact with) the abdomen 102 of the subject, whereas the cover 106 of the device 100 has no contact with the abdomen 102 of the subject. The rigid base 104 is configured such that, in use, it provides a separation between the cover 106 and the abdomen 102 of the subject. Thus, in use, the cover 106 of the device 100 is separated from the abdomen 102 of the subject by the rigid base 104.

As illustrated in FIGS. 1A and 1B, the device 100 comprises a fetal heart rate sensor 108. The fetal heart rate sensor 108 is mounted on the rigid base 104. The fetal heart rate sensor 108 may be located within the device 100, as illustrated in FIGS. 1A and 1B, or outside (such as on an external surface of) the device 100. The fetal heart rate sensor 108 is configured to measure the fetal heart rate. The device 100 also comprises a uterine contractions sensor 110 (which may also be referred to as a tocodynamometer sensor). The uterine contractions sensor 110 is located within the device 100 and is configured to measure the uterine contractions of the subject.

As the fetal heart rate sensor 108 is mounted on the rigid base 104 and the rigid base 104 is for placement on the abdomen 102 of the subject, the fetal heart rate sensor 108 is located at a part of the device 100 that is for placement on the abdomen 102 of the subject. In some embodiments, the uterine contractions sensor 110 may also be located at a part of the device 100 that is for placement on the abdomen 102 of the subject, such as mounted on the rigid base 104 of the device 100. In other embodiments, such as that illustrated in FIG. 1A, the uterine contractions sensor 110 can be located at an opposing part of the device 100 to the part of the device 100 that is for placement on the abdomen 102 of the subject (or a part of the device 100 that is opposite to the part of the device 100 for placement on the abdomen 102 of the subject). For example, the uterine contractions sensor 110 may be mounted on the cover 106 of the device 100, which is opposite to the rigid base 104 of the device 100 for placement on the abdomen 102 of the subject. In yet other embodiments, such as that illustrated in FIG. 1B, the uterine contractions sensor 110 may be mounted in a space between the rigid base 104 and the cover 106. For example, the uterine contractions sensor 110 may be mounted on a supporting member that extends into the space between the rigid base 104 and the cover 106.

Although some examples have been provided for the location of the uterine contractions sensor 110 within the device 100, it will be understood that other examples are also possible and the uterine contractions sensor 110 can, in fact, be located at any position within the device 100.

In any of the embodiments described herein, the uterine contractions of the subject can be measured by the uterine contractions sensor 110 as a reaction of the flexible portion of the device 100 to the uterine contractions of the subject, which is equal to an action of the uterine contractions of the subject at the rigid base 104 of the device 100 for placement on the abdomen 102 of the subject. This allows an optimised and uninfluential arrangement. Also, the location of the fetal heart rate sensor 108 can be maintained or kept unchanged.

The uterine contractions sensor 110 referred to herein can be any sensor configured to measure a variation in a property representative of uterine contractions. The variation in the property is a variation caused by movement of the flexible portion of the device 100 in response to the uterine contractions. The uterine contractions sensor 110 can be a non-mechanical sensor. More specifically, the uterine contractions sensor 110 can be any sensor capable of measuring uterine contractions without the need for additional mechanical components. The uterine contractions sensor 110 can, for example, comprise any one or more of a pressure sensor, an optical sensor, a capacitive sensor, an inductive sensor, or any other sensor suitable for measuring uterine contractions, or any combination of sensors suitable for measuring uterine contractions. In embodiments where the uterine contractions sensor 110 comprises a pressure sensor, the pressure sensor is configured to measure a variation or change in pressure representative of (and caused by) the uterine contractions. For example, the pressure sensor can measure tension variations or changes in the uterine muscle of the subject caused by the uterine contractions as a variation or change in pressure. A variation or change in pressure occurs, for example, due to the compression and/or subsequent decompression of a volume of gas enclosed within the device 100. The pressure force resulting from the compression and/or subsequent decompression of the volume of gas enclosed within the device 100 can be measured by the pressure sensor. In some embodiments, the pressure sensor may comprise a micro-electro-mechanical systems (MEMS) based pressure sensor. In this way, the size of the device 100 can be reduced.

In embodiments where the uterine contractions sensor 110 comprises an optical sensor, the optical sensor is configured to measure a variation or change in light intensity representative of (and caused by) the uterine contractions. For example, the tension variations or changes in the uterine muscle of the subject caused by the uterine contractions can be measured by the optical sensor as a variation or change in light intensity. In an example optical sensor embodiment, the optical sensor may comprise a light source mounted on the rigid base 104 and positioned to emit light toward the flexible portion and a light detector also mounted on the rigid base 104 and positioned to detect light reflected from the flexible portion. In some of these embodiments, the flexible portion may comprise a reflective material. For example, at least part of the flexible portion may be formed from a reflective material or the flexible portion may be at least partially coated with a reflective material.

In embodiments where the uterine contractions sensor 110 comprises a capacitive sensor, the capacitive sensor is configured to measure a variation or change in capacitance representative of (and caused by) the uterine contractions. For example, the tension variations or changes in the uterine muscle of the subject caused by the uterine contractions can be measured by the capacitive sensor as a variation or change in capacitance. In an example capacitive sensor embodiment, the capacitive sensor may comprise a pair of conductors. For example, the rigid base 104 of the device 100 may comprise one of the pairs of conductors and the cover 106 of the device 100 may comprise the other of the pairs of conductors. That is, the rigid base 104 can comprise one conductor of the pair of conductors and the cover 106 can comprise the other conductor of the pair of conductors.

In embodiments where the uterine contractions sensor 110 comprises an inductive sensor, the inductive sensor is configured to measure a variation or change in inductance representative of (and caused by) the uterine contractions of the subject. For example, the tension variations or changes in the uterine muscle of the subject caused by the uterine contractions can be measured by the inductive sensor as a variation or change in inductance. In an example inductive sensor embodiment, the inductive sensor may comprise a pair of inductors. For example, the rigid base 104 of the device 100 may comprise one of the pairs of inductors and the cover 106 of the device 100 may comprise the other of the pairs of inductors. That is, the rigid base 104 can comprise one inductor of the pair of inductors and the cover 106 can comprise the other inductor of the pair of inductors. In another example inductive sensor embodiment, the inductive sensor may comprise a coil and a conductive (for example, metallic) plate.

Although some examples have been provided for the type of uterine contractions sensor 110, it will be understood that other examples are also possible and the uterine contractions sensor 110 can, in fact, comprise any sensor that is suitable for measuring uterine contractions, or any combination of sensors that are suitable for measuring uterine contractions.

In any of the embodiments described herein, either parts of or the entire fetal heart rate sensor 108 and either parts of or the entire uterine contractions sensor 110 may be placed on or connected to a printed circuit board (PCB). In some embodiments, the fetal heart rate sensor 108 and/or the uterine contractions sensor 110 may comprise a computing and/or communications interface (for example, circuitry or a digital interface) for connection to one or more other components (such as a processor, which will be described in more detail later).

In some embodiments, the device 100 described herein can be airtight (or substantially airtight) or watertight (or substantially watertight). This has the advantageous effect that the device 100 can be used in underwater applications. In some of these embodiments, the uterine contractions sensor 110 may comprise at least a pressure sensor. In some embodiments, the device 100 may be tested to determine whether it is watertight or airtight (or sufficiently watertight or airtight) by way of a vacuum measurement, for example, in a testing stage. In some embodiments, the rigid base 104 of the device 100 for placement on the abdomen 102 of the subject can be made of a different material to the cover 106 of the device 100 or a different material to the flexible portion of the device 100 (in which case, the rest of the cover 106 of the device 100 may be made of the same material as the rigid base 104). For example, the rigid base 104 of the device 100 for placement on the abdomen 102 of the subject can be made of a material that is stronger, more resilient, more resistant, and/or harder than a material of the cover 106 of the device or than the material of the flexible portion of the device 100. This can be beneficial in case the rigid base 104 of the device 100 for placement on the abdomen 102 of the subject comes into contact with aggressive liquids (such as aggressive disinfection liquids), which can damage soft material and may cause a leak in the device 100. Thus, the device 100 is sensitive to uterine contractions by virtue of the cover 106 of the device 100 comprising a flexible portion that is moveable in response to uterine contractions of the subject and the device 100 is also more robust.

In any of the embodiments described herein, a part of the device 100 that is rigid (such as the base 104 of the device 100 and optionally also a portion of the cover 106 of the device 100) may be a part that maintains its structure responsive to uterine contractions. For example, a part of the device 100 that is rigid may maintain its structure irrespective of a force generated by the uterine contractions. A part of the device 100 that is rigid may, for example, be a part of the device 100 that is hard, non-deformable and/or non-flexible. In some embodiments, a part of the device 100 that is rigid can be a part of the device 100 that is formed of a rigid material (for example, an inelastic material such as a hard plastic, polyphenylsulfon PPSU, glass fiber reinforced acrylnitril-butadien-styrol-copolymere ABS, or any other rigid material). According to some embodiments, the rigid material may, for example, be a composite material. In any of the embodiments described herein, the flexible portion of the device 100 that is moveable may be a portion that is deformable or flexible. In some embodiments, for example, the flexible portion of the device 100 that is moveable can be a portion that is formed of a material that is soft, deformable and/or flexible (for example, an elastomer or elastic material such as rubber, polyurethane PUR, polyimide PU, or any other soft, deformable and/or flexible material). According to some embodiments, the soft, deformable and/or flexible material may, for example, be a composite material.

In some embodiments, the entire cover 106 of the device 100 may be the flexible portion. In other embodiments, the cover 106 of the device 100 may comprise an aperture in which or across which a flexible portion is disposed. For example, the flexible portion may comprise a flexible surface, such as a flexible membrane, located in or across the aperture of the cover 106 of the device 100. The aperture of the cover 106 of the device 100 may optionally be surrounded by a groove, such as an annular groove. At least the portion of the cover 106 surrounding the aperture may be rigid. Alternatively or in addition to the cover 106 of the device 100 comprising an aperture across which a flexible portion is disposed, a flexible portion may extend around the periphery of the cover 106 of the device 100 according to some embodiments. In these embodiments, the flexible portion extending around the periphery of the cover 106 of the device 100 may be configured to be connected to the rigid base 104 of the device 100. Thus, in some embodiments, the device 100 may have a concertina arrangement, where the flexible portion is positioned between the cover 106 and the rigid base 104 (for example, as a flexible band). In some of these embodiments, both the base 104 and the cover 106 between which the flexible portion is positioned may be rigid.

In some embodiments, a sensitivity of the uterine contractions sensor 110 may be adjustable depending on an extent of the flexible portion that is moveable and/or an enclosed volume of gas inside the device 100. Although only a single flexible portion may be provided according to some embodiments, it is also possible for there to be multiple flexible portions according to other embodiments. As mentioned earlier, a uterine contraction comprises a hardening or tensing of the uterine muscle, which causes a force on the device 100 placed on the abdomen 102 of the subject. More specifically, the force acts on the flexible portion of the device 100. This force causes movement of the flexible portion and the flexible portion thus reduces the volume of gas inside the device 100 through compression of the gas.

Figure 2:
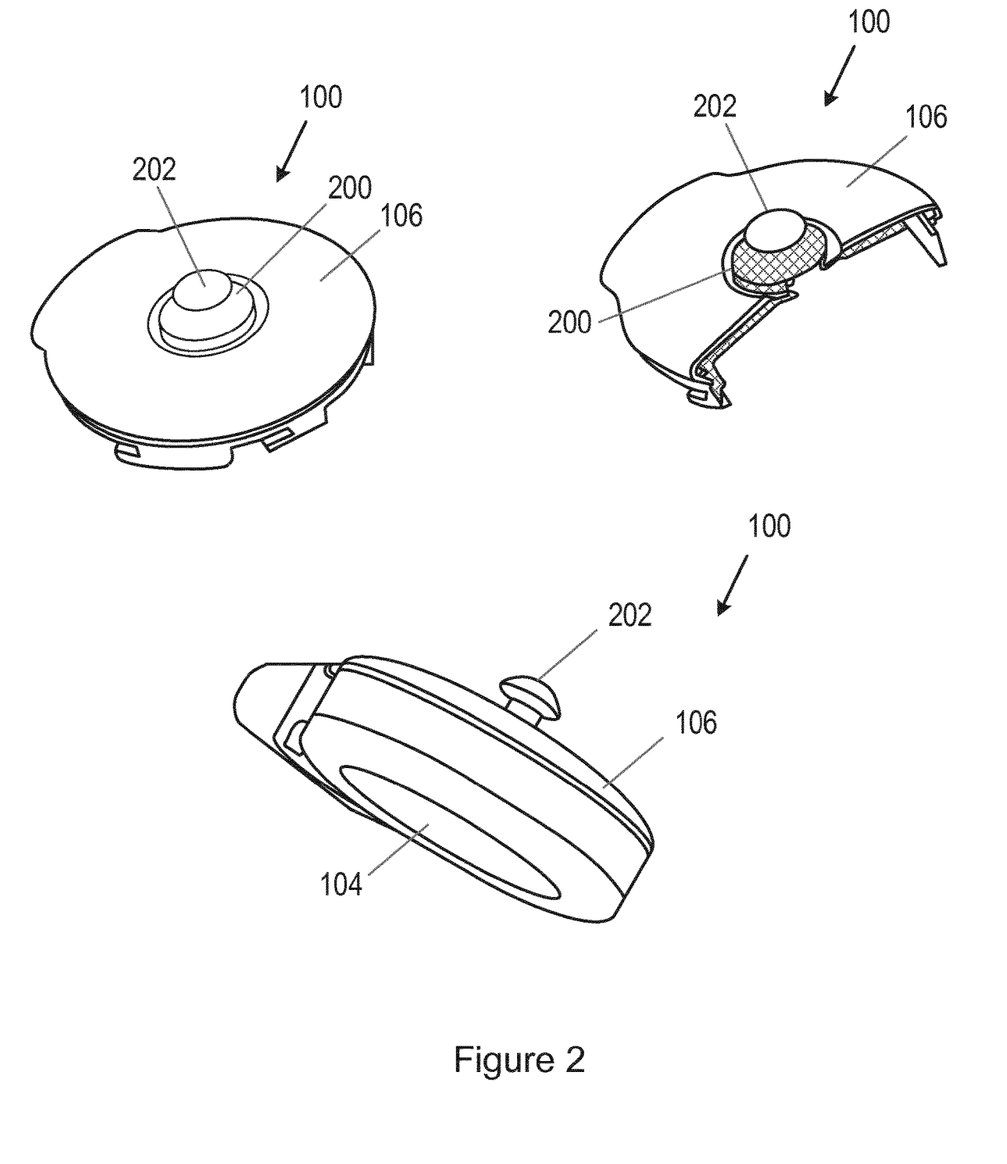
FIG. 2 is an illustration of a device according to an embodiment.

FIG. 2 illustrates an example of the device 100 for placement on the abdomen 102 of a subject to measure uterine contractions of the subject and a fetal heart rate according to an embodiment. The device 100 comprises a rigid base 104 for placement on the abdomen 102 of the subject and a cover 106 configured to connect to the rigid base 104. The cover 106 of the device 100 comprises a flexible portion 200 that is moveable responsive to the uterine contractions.

In this illustrated example embodiment, the cover 106 of the device 100 comprises an aperture across which the flexible portion 200 is disposed. More specifically, the flexible portion 200 in this illustrated example embodiment comprises a flexible surface (such as a flexible membrane) located across the aperture in the cover 106 of the device 100. In this illustrated example embodiment, the aperture is surrounded by an annular groove. The flexible portion 200 is located across the aperture on the inside of the device 100. More specifically, in this illustrated example embodiment, the flexible portion 200 covers the entire internal surface of the cover 106 of the device. The flexible portion 200 in this illustrated example embodiment also extends through the aperture to protrude above the surface of the cover 106 of the device 100.

The device 100 according to this illustrated example embodiment also comprises a rigid button 202. The rigid button 202 is located at the aperture of the cover 106 of the device 100 and is connected to the cover 106 of the device 100 by the flexible portion 200 (or, more specifically, by the part of the flexible portion 200 that extends through aperture). The rigid button 202 also protrudes above the surface of the cover 106 of the device 100. A purpose of the rigid button 202 is for attachment of the device 100 to a supporting member (such as a belt, a strap, or any other supporting member) that is configured to be worn around the abdomen 102 of the subject to hold the device 100 against the abdomen 102 of the subject and which will be described in more detail later. However, it will be understood that this is only one example embodiment of the device 100 and, in other example embodiments, the rigid button 202 may not be present and the device 100 may be held in place against the abdomen 102 of the subject in another way.

In some embodiments where the device comprises a rigid button 202, an end of the rigid button 202 may extend into the internal volume of the device 100. In these embodiments, where the uterine contractions sensor 110 comprise an optical sensor, the end of the rigid button 202 that extends into the internal volume of the device 100 may comprise a reflective surface. For example, a light source may be mounted on the rigid base 104 and positioned to emit light toward the reflective surface of the rigid button 202. A light detector may also be mounted on the rigid base 104 and positioned to detect light reflected from the reflective surface of the rigid button 202. As the rigid button 202 is connected to the cover 106 of the device 100 by the flexible portion 200, movement of the flexible portion 200 responsive to uterine contractions in turn causes movement of the rigid button 202, such that a variation in light intensity represen- tative of uterine contractions is detected at the light detector. However, it will be understood that this is only one example of the manner in which uterine contractions may be measured and, in other examples, the device 100 may comprise any other sensor or sensors configured to measure the uterine contractions.

In the illustrated example embodiment of FIG. 2, aside from the flexible portion 200 that is moveable, the cover 106 of the device 100 and the base 104 of the device 100 are rigid (for example, formed of a hard material such as a hard plastic). Although not illustrated in FIG. 2, the fetal heart rate sensor 108 is mounted on the rigid base 104 within the device 100, where the rigid base 104 is for placement on the abdomen 102 of the subject. The uterine contractions sensor 110 is also located within the device 100. In the illustrated example embodiment, the force on the device 100 caused by the uterine contractions moves the flexible portion 200 relative to the rigid base 104 of the device 100 and this movement of the flexible portion 200 compresses the volume of gas inside the device 100.

Figure 3:
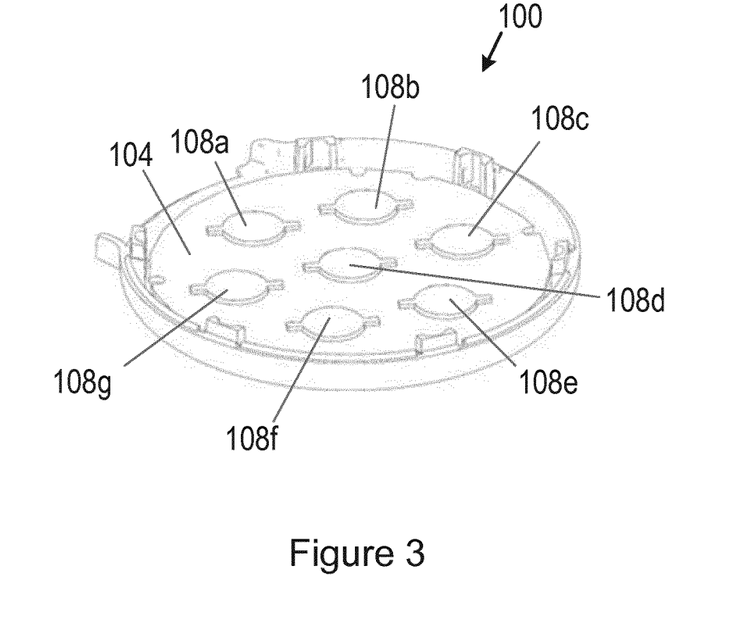
FIG. 3 is an illustration of a part of a device according to an embodiment.

FIG. 3 illustrates an example of the device 100 comprising a rigid base 104 adapted for placement on the abdomen 102 of the subject at which the fetal heart rate sensor 108 is located. In this illustrated example embodiment, the fetal heart rate sensor 108 comprises a plurality of sensing elements 108a, 108b, 108c, 108d, 108e, 108f, 108g. Although the device 100 according to this example embodiment comprises seven sensing elements, it will be understood that any other number of sensing elements is also possible. In some embodiments, the plurality of sensing elements can be located equidistant from each other or can be equally spaced. For illustration purposes, only the rigid base 104 of the device 100 for placement on the abdomen 102 is shown in FIG. 3. However, it will be understood that the device 100 also comprises the cover 106 and the uterine contractions sensor 110.

In some embodiments, the fetal heart rate sensor 108 described herein can be an ultrasound sensor. In some embodiments, the ultrasound sensor 108 may comprise a plurality of ultrasound sensing elements 108a, 108b, 108c, 108d, 108e, 108f, 108g (for example, arranged as illustrated in FIG. 3). In some of these embodiments, the plurality of ultrasound sensing elements may be located equidistant from each other or may be equally spaced. This can, for example, provide a more homogeneous sound field. Although an example has been provided for the type of fetal heart rate sensor 108 that the device 100 may comprise, it will be understood that any other type of sensor or any combinations of sensors suitable for measuring a fetal heart rate are also possible. For example, another example of a fetal heart rate sensor 108 is a microphone and the person skilled in the art will also be aware of other sensors that may be used for fetal heart rate measurement.

In some embodiments, the device 100 may comprise a single fetal heart rate sensor 108 while, in other embodiments, the device 100 may comprise a plurality of fetal heart rate sensors 108. In embodiments where the device 100 comprises a plurality of fetal heart rate sensors 108, the plurality of fetal heart rate sensors 108 may be mounted at different positions on the rigid base 104 and each fetal heart rate sensor 108 can be configured to measure the fetal heart rate. Similarly, in some embodiments, the device 100 may comprise a single uterine contractions sensor 110 while, in other embodiments, the device 100 may comprise a plurality of uterine contractions sensors 110. In embodiments where the device 100 comprises a plurality of uterine contractions sensors 110, the plurality of uterine contractions sensors 110 may be located at different positions within the device 100 and each uterine contractions sensor 110 may be configured to measure the uterine contractions.

In any of the embodiments described herein, the cover 106 of the device 100 may be removable from the rigid base 104 of the device 100. Thus, the cover 106 of the device 100 can be interchangeable according to some embodiments. This is advantageous since the cover 106 of the device 100 and/or the uterine contractions sensor 110 located within the device 100 can be replaced without having to also replace the rigid base 104 of the device 100 on which the fetal heart rate sensor 108 is mounted. Similarly, the rigid base 104 of the device 100 on which the fetal heart rate sensor 108 is mounted can be replaced without having to also replace the cover 106 of the device 100 and/or the uterine contractions sensor 110 located within the device 100.

There is thus provided herein an improved device 100 for measuring uterine contractions of the subject and a fetal heart rate. There is also provided a method of operating the device 100 described herein, when placed on the abdomen 102 of a subject, to measure uterine contractions of the subject and a fetal heart rate. The method comprises controlling the fetal heart rate sensor 108 to measure the fetal heart rate. Alternatively or in addition, the method comprises controlling the uterine contractions sensor 110 to measure the uterine contractions. In some embodiments where both the fetal heart rate and the uterine contractions are measured, the sensors 108, 110 may be configured to measure the fetal heart rate and the uterine contractions simultaneously. For example, the fetal heart rate sensor 108 may be controlled to measure the fetal heart rate and the uterine contractions sensor 110 may be controlled to measure the uterine contractions simultaneously.

According to some embodiments, a processor (not illustrated) may be configured to control the fetal heart rate sensor 108 to measure the fetal heart rate and the uterine contractions sensor 110 to measure the uterine contractions in the manner described herein. Although not illustrated in the figures, in some embodiments, the device 100 may comprise the processor. In other embodiments, the processor may be external to (i.e. separate to or remote from) the device 100. For example, the processor may be part of another device. The processor can comprise one or more processors (such as one or more microprocessors MPUs), one or more processing units, one or more multi-core processors and/or one or more controllers (such as one or more microcontrollers MCU), that are configured or programmed to control the fetal heart rate sensor 108 to measure the fetal heart rate and the uterine contractions sensor 110 to measure the uterine contractions in the manner described herein. In particular implementations, the processor can comprise a plurality of software and/or hardware modules, each configured to perform, or that are for performing, individual or multiple steps of the method described herein in relation to the device 100.

Although also not illustrated in the figures, in some embodiments, the device 100 may comprise a communications interface (or circuitry). The communications interface can be for enabling the device 100 to communicate with (or connect to) one or more other devices. For example, in embodiments where a processor is external to (i.e. separate to or remote from) the device 100, the processor may control the fetal heart rate sensor 108 to measure the fetal heart rate and/or the uterine contractions sensor 110 to measure the uterine contractions via the communications interface. The communications interface may be configured to communicate wirelessly, via a wired connection, or via any other communication (or data transfer) mechanism. In some wireless embodiments, the communications interface may, for example, use radio frequency (RF), Bluetooth, or any other wireless communication technologies, for communications. In some embodiments, the device 100 may transfer measurements (or data or information) to one or more other devices. For example, the device 100 may transfer a measured fetal heart rate and/or measured uterine contractions to one or more other devices. In these embodiments, the measurements (or data or information) can be transferred via the communications interface.

Although the device 100 has been described herein as comprising certain components, it will be appreciated that the device 100 may equally comprise additional or alternative components to those described earlier. For example, in some embodiments, the device 100 may comprise a battery or other power supply for powering the device 100 or means for connecting the device 100 to a mains power supply, or any other component, or any combination of components.

Figure 4:
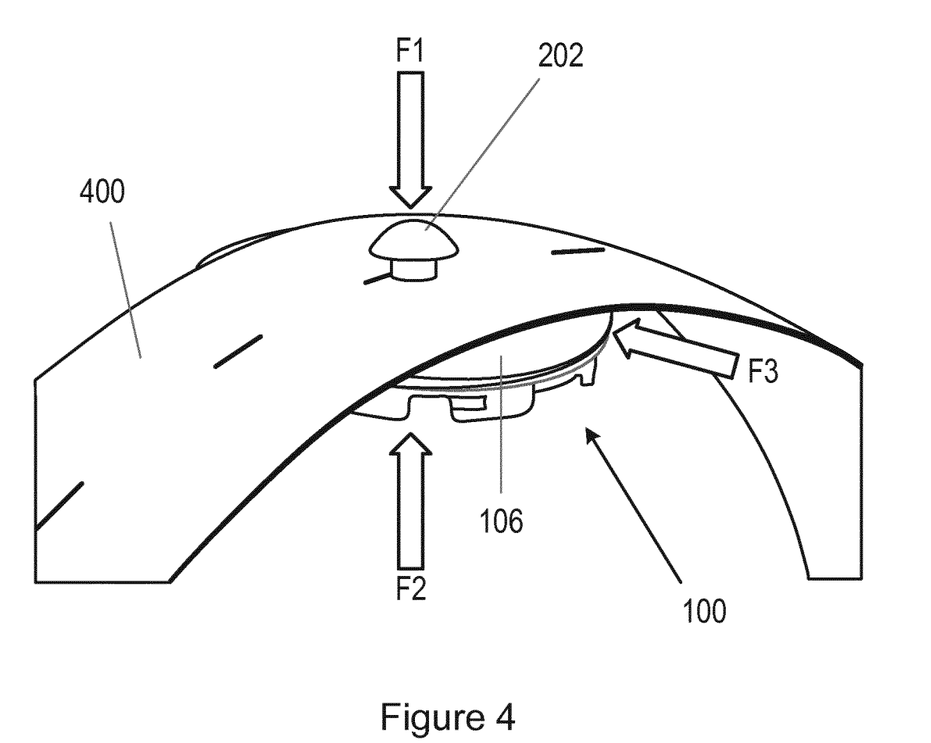
FIG. 4 is an illustration of a part of a device in use according to an embodiment.

FIG. 4 is an illustration of a device 100 for placement on the abdomen 102 of a subject to measure uterine contractions of the subject and a fetal heart rate in use according to an example embodiment. As illustrated in FIG. 4, in some embodiments, the device 100 described herein may be attachable to a supporting member (such as a belt, a strap, or any other supporting member) 400 that is configured to be worn on (or around) the abdomen 102 of the subject. The device 100 can be configured to be held against the abdomen 102 of the subject by the supporting member 400. Thus, the supporting member 400 can hold the device 100 in place on (or fix the device 100 to) the abdomen 102 of the subject. The supporting member 400 can, for example, be configured to extend around the torso of the body of the subject at the abdomen 102. The supporting member 400 may be formed from, or may comprise, an elastic material. The supporting member 400 can be further configured to contact with the device 100 to cause movement of the flexible portion in response to the uterine contractions. While the rigid base 104 has skin contact with the abdomen 102 of the subject when the device 100 is in use, the cover 106 has no skin contact with the abdomen 102 of the subject. In this illustrated example embodiment, the cover 106 instead has contact with the supporting member 400.

In the example embodiment illustrated in FIG. 4, the device 100 is of the form illustrated in FIG. 2. However, it will be understood that the device 100 may take other forms and still be attachable to a supporting member 400 (such as that illustrated in FIG. 4 or any other type of supporting member) by any suitable attachment mechanism. In the example embodiment illustrated in FIG. 4, the rigid button 202 of the device 100 is placed through a hole (for example, a buttonhole or slit) in the supporting member 400. In this way, the supporting member 400 can be secured to the device 100. The rigid button 202 can thus be used to keep the device 100 in place. In some embodiments, the device 100 may be centred on the supporting member 400 to ensure a defined force transmission.

As illustrated in the example embodiment of FIG. 4, in order to hold the device 100 at a certain location on the abdomen 102 of the subject, a force F1 is necessary that forces the device 100 onto the abdominal wall of the subject. In this illustrated example embodiment, this force is generated by the supporting member 400, which keeps the device 100 in place on the abdomen 102 of the subject. In order to prevent the device 100 from moving, an equal counterforce F2 is required, which is produced by the elasticity of the abdominal wall of the subject. In case of a uterine muscle contraction, a third force F3 is generated and this force increases the counterforce F2. To keep the device 100 at rest, the supporting member 400 balances this force. As a consequence, the force F1 that forces the device 100 onto the abdominal wall and the counterforce F2 are always the same. For this reason, the force caused by uterine contractions can be measured by the uterine contractions sensor 110 located within the device 100.

Although an example embodiment has been described with reference to FIGS. 2 and 4 where the device 100 comprises a rigid button 202 for attaching the device 100 to a supporting member 400, a person skilled in the art will be aware of other mechanisms for attaching the device 100 to a supporting member 400 (such as that shown in FIG. 4). For example, instead of a rigid button 202, the device 100 may comprise a clip (such as an adaptor clip) for attaching the device 100 to a supporting member 400. More specifically, the cover 106 of the device 100 may comprise the clip. In other embodiments, the device 100 may simply be placed between the supporting member 400 and the abdomen 102 of the subject. Also, although some examples have been provided for the manner in which the device 100 may be held in place on the abdomen 102 of the subject, other examples are also possible and the person skilled in the art will be aware of these other examples.

Figure 5:
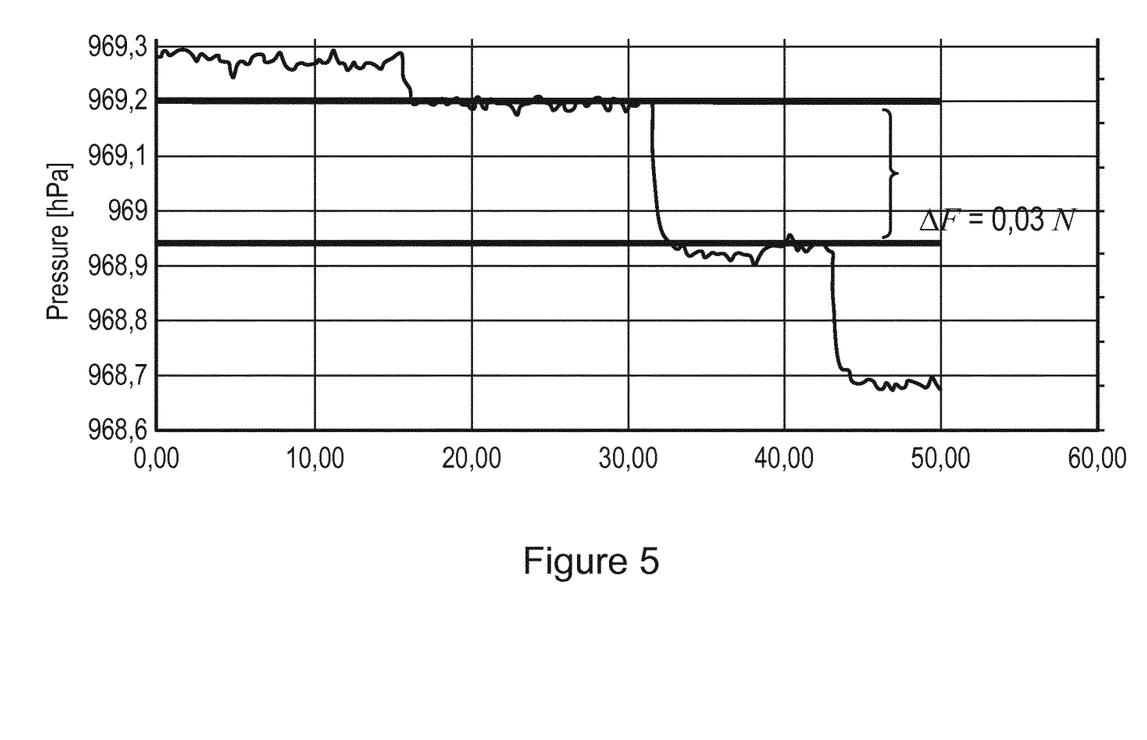
FIG. 5 is a graphical representation of a variation in pressure measured by a device according to an embodiment.

FIG. 5 is a graphical representation of a variation in pressure measured by a uterine contractions sensor 110 over time of a device 100 according to an embodiment. In this illustrated embodiment, the uterine contractions sensor 110 of the device 100 is thus a pressure sensor configured to measure a variation in pressure representative of uterine contractions. As illustrated in FIG. 5, the pressure sensor is able to detect a variation in pressure with a sufficient resolution. In the illustrated embodiment, force increments of 0.025N are generated by simulated uterine contractions while testing the device 100. The variation in pressure ΔF is measured as 0.03N in this illustrated embodiment, which indicates that the pressure sensor is able to provide values with a sufficient accuracy and a significant step spacing.

There is thus provided herein an improved device 100 and a method of operating the improved device 100 for measuring uterine contractions of a subject and a fetal heart rate. The device and method described herein can, for example, be useful in monitoring a subject and a fetus during pregnancy, labour and delivery.

There is further provided a computer program product comprising a computer readable medium, the computer readable medium having computer readable code embodied therein, the computer readable code being configured such that, on execution by a suitable computer or processor, the computer or processor is caused to perform the method described herein. More specifically, on execution by a suitable computer or processor, the computer or processor can be caused to operate the device according to the method described herein.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A device for placement on the abdomen of a subject to measure uterine contractions of the subject and a fetal heart rate, the device comprising:
    a rigid base for placement on the abdomen of the subject;
    a cover configured to connect to the rigid base, wherein the cover has no contact with the abdomen of the subject when the rigid base is placed on said abdomen and comprises a flexible portion moveable in response to uterine contractions of the subject, said rigid base and cover providing a casing of the device;
    a fetal heart rate sensor mounted on the rigid base and configured to measure the fetal heart rate; and
    a uterine contractions sensor located within the device and configured to measure the uterine contractions of the subject as a reaction of the flexible portion to said uterine contractions.

2. The device as claimed in claim 1, wherein:
    the entire cover is the flexible portion; or
    the cover comprises an aperture across which the flexible portion is disposed; or
    the flexible portion extends around the periphery of the cover and is configured to be connected to the rigid base.

3. The device as claimed in claim 1, wherein the uterine contractions sensor comprises any one or more of:
    a pressure sensor configured to measure a variation in pressure representative of uterine contractions;
    an optical sensor configured to measure a variation in light intensity representative of uterine contractions;
    a capacitive sensor configured to measure a variation in capacitance representative of uterine contractions; and
    an inductive sensor configured to measure a variation in inductance representative of uterine contractions.

4. The device as claimed in claim 3, wherein the optical sensor comprises:
    a light source mounted on the rigid base and positioned to emit light toward the flexible portion; and
    a light detector mounted on the rigid base and positioned to detect light reflected from the flexible portion.

5. The device as claimed in claim 3, wherein:
    the capacitive sensor comprises a pair of conductors;
    and the rigid base comprises one conductor of the pair of conductors; and
    the cover comprises the other conductor of the pair of conductors.

6. The device as claimed in claim 3, wherein:
    the inductive sensor comprises: (1) a coil and a conductive plate; or (2) a pair of inductors;
    the rigid base comprises one inductor of the pair of inductors; and
    the cover comprises the other inductor of the pair of inductors.

7. The device as claimed in claim 1, wherein the fetal heart rate sensor comprises an ultrasound sensor or a microphone.

8. The device as claimed in claim 1, wherein the device comprises a plurality of fetal heart rate sensors mounted at different positions on the rigid base, each fetal heart rate sensor configured to measure the fetal heart rate.

9. The device as claimed in claim 1, wherein the device comprises a plurality of uterine contractions sensors located at different positions within the device, each uterine contractions sensor configured to measure the uterine contractions.

10. The device as claimed in claim 1, wherein the cover is removable from the rigid base.

11. The device as claimed in claim 1, wherein the device is substantially airtight or substantially watertight.

12. The device as claimed in claim 1, wherein the device is configured to be held against the abdomen of the subject by a supporting member, wherein the supporting member is configured to be worn around the abdomen of the subject and further configured to contact with the device to cause movement of the flexible portion in response to the uterine contractions.

13. The device as claimed in claim 1, wherein the sensors are configured to measure the fetal heart rate and the uterine contractions simultaneously.

14. The method of operating a device, when placed on the abdomen of a subject, to measure uterine contractions of the subject and a fetal heart rate, wherein the device is as claimed in claim 1 and wherein the method comprises:
   controlling the fetal heart rate sensor to measure the fetal heart rate; and/or
   controlling the uterine contractions sensor to measure the uterine contractions.

15. The computer program product comprising a computer readable medium, the computer readable medium having computer readable code embodied therein, the computer readable code being configured such that, on execution by a suitable computer or processor, the computer or processor is caused to operate the device according to the method as claimed in claim 14.

\* \* \* \* \*